United States Patent
Petri et al.

(10) Patent No.: US 6,519,535 B1
(45) Date of Patent: Feb. 11, 2003

(54) EDDY CURRENT TECHNIQUE FOR PREDICTING BURST PRESSURE

(75) Inventors: Mark C. Petri, Yorkville, IL (US); David S. Kupperman, Oak Park, IL (US); James A. Morman, Woodridge, IL (US); Jaques Reifman, Western Springs, IL (US); Thomas Y. C. Wei, Downers Grove, IL (US)

(73) Assignee: The University of Chicago, Chicago, IL (US)

( * ) Notice: Subject to any disclaimer, the term of this patent is extended or adjusted under 35 U.S.C. 154(b) by 167 days.

(21) Appl. No.: 09/587,008

(22) Filed: Jun. 5, 2000

(51) Int. Cl.$^7$ .................................................. G01L 1/00
(52) U.S. Cl. .............................. 702/42; 702/38; 702/39; 73/592; 706/21
(58) Field of Search ............................... 702/33–36, 38, 702/39, 42, 43, 57, 108, 113, 114, 140, 181, 183, 184, 188; 73/360, 40.5 A, 587, 592; 706/21, 22; 324/222, 223, 226, 241

(56) References Cited

U.S. PATENT DOCUMENTS

| | | | | |
|---|---|---|---|---|
| 4,763,274 A | * | 8/1988 | Junker et al. ................ | 324/220 |
| 5,339,256 A | * | 8/1994 | Levy et al. .................... | 702/38 |
| 5,455,777 A | * | 10/1995 | Fujiyama et al. ............. | 702/34 |
| 5,737,445 A | * | 4/1998 | Oppenlander et al. ....... | 324/238 |
| 5,898,304 A | * | 4/1999 | Mandl .......................... | 324/202 |
| 6,115,674 A | * | 9/2000 | Brudnoy et al. .............. | 702/38 |

OTHER PUBLICATIONS

Udpa, L. & Udpa, S.S., "Neural networks for the classification of nondestructive evaluation signals", IEEE Proceedings Radar and Signal Processing, Feb. 1991, vol. 138, No. 1, pp. 41–45.*

Chen et al, "A Novel Signal Processing Technique for Eddy–Current Testing of Steam Generator Tubes", IEEE Transactions on Magnetics, May 1998, vol. 34, No. 3, pp. 642–648.*

Angeli et al, "Classification of Eddy Current NDT Data by Probablistic Neural Networks", International Joint Conference on Neural Networks, Jul. 1999, vol. 6, pp. 4012–4014.*

* cited by examiner

Primary Examiner—Marc S. Hoff
Assistant Examiner—Marc Cooley
(74) Attorney, Agent, or Firm—Michael D. Rechtin; Foley & Lardner

(57) ABSTRACT

A signal processing technique which correlates eddy current inspection data from a tube having a critical tubing defect with a range of predicted burst pressures for the tube is provided. The method can directly correlate the raw eddy current inspection data representing the critical tubing defect with the range of burst pressures using a regression technique, preferably an artificial neural network. Alternatively, the technique deconvolves the raw eddy current inspection data into a set of undistorted signals, each of which represents a separate defect of the tube. The undistorted defect signal which represents the critical tubing defect is related to a range of burst pressures utilizing a regression technique.

11 Claims, 7 Drawing Sheets

LOBE LENGTH = $L_1 + L_2$
VERTICAL VOLTAGE HEIGHT = $H_1 + H_2$

EDDY CURRENT TECHNIQUE FOR PREDICTING BURST PRESSURE

This invention was made with Government support under Contract No. W-31-109-ENG-38 awarded by the U.S. Department of Energy. The Government has certain rights in this invention.

FIELD OF THE INVENTION

The present invention relates to a method for predicting burst pressures in tubing. More particularly this invention relates to a method for predicting burst pressures in thin-walled tubing by deconvolving eddy current data to identify electrical characteristics of tubing defects and analyzing the deconvolved data using artificial neural network modeling to predict burst pressures.

BACKGROUND OF THE INVENTION

Steam generators have a long history of being a troublesome major component in pressurized water reactor nuclear power plants, and steam generator tube failures remain a costly concern for nuclear utilities. The thousands of thin-walled tubes of a steam generator form a containment boundary between the high-pressure primary and low-pressure secondary water systems. Therefore, plant operators must repair or plug tubes if significant cracking is detected. Tube cracking has directly led to the decommissioning and replacement of many U.S. steam generators. Eddy current (EC) techniques are currently the predominant technology used for the in-service inspection of nuclear power plant steam generator tubing in the U.S. and elsewhere. Current EC measurement techniques using differential bobbin-coil probes are extremely sensitive to the presence of axial cracks in the tube wall, but they are equally sensitive to the presence of tubing artifacts, i.e. tube dents, fretting, support structures, and corrosion products. EC signal interpretation is further complicated by cracking geometries more complex than a single axial crack. Since cracks are difficult to distinguish from artifacts and even more difficult to characterize, operators are often forced to repair or plug a tube upon detection of a defect, regardless of its effect on tube integrity.

Current analysis techniques based on EC bobbin-probe measurements have been relatively successful in detecting cracks, but fail almost completely when applied to the characterization of cracks and their effect on tube integrity. For example, EC inspection software is available to linearly mix signals taken at different frequencies. These mixing algorithms can accentuate signals from defects, aiding defect detection, but signal distortions due to mixing make this technique less useful for defect sizing. Since they respond only to an aggregate disruption of electrical current along the circumference of a tube at a given axial position, bobbin coils cannot differentiate multiple defects along the tube circumference. Bobbin probes, therefore, are ineffective for characterizing complex cracking. Some limited success has been demonstrated using rotating pancake coils to estimate crack depth. This invention emphasizes the use of differential bobbin coils, but is not limited to that technique.

Additionally, EC signals from cracks, wastage, and other physical sources have similar, if not identical, frequency responses. Frequency-based signal processing techniques such as Fourier filtering and wavelet transformations are ineffective at winnowing out artifact signals, since their frequency signatures are indistinguishable from those of crack signals.

Likewise, algorithms based on EC expert rules applied to the identification of defects in steam generator and heat exchanger tubing have met with only limited success. Attempts to use expert systems to estimate the depth of steam generator tubing flaws in tube support plate regions based on EC voltages and phase angles have met with even less success because complex defect morphologies have limited the accuracy of those algorithms to only ±20 % of the tube wall thickness. Thus, current EC-based expert rules have resulted in poor decisions about whether to plug suspect steam generator tubes.

Artificial intelligence methods have held the promise of providing improved modeling of tube defects compared to conventional empirical modeling techniques. Beginning in the late 1970s, pattern-recognition algorithms have been used to determine which EC Lissajous-pattern features best correlated with the defect classification of tubes with electrodischarge-machined (EDM) slots, machined elliptical wastage, and uniform thinning. These parametric studies considered many signal features based on the shape of the Lissajous figures and ones based on EC voltage readings. Along with classifying the simulated flaws, the researchers attempted to predict the depth of the uniform thinning based on a least-squares regression of EC features. However, these attempts to predict the size of the axial slots were largely unsuccessful.

More recently, an artificial intelligence technique of case-based reasoning has been applied to the classification and characterization of flaws detected through EC inspection and other nondestructive examination methods. Case-based reasoning relies on a comparison of input features (e.g. as from an eddy current measurement) to values used previously for training the system. Cases with similar input features would be expected to have similar solutions. Although case-based reasoning has potential advantages over other artificial intelligence techniques, it still has limitations, including the requirement of a large data base to cover the range of possible input-feature combinations, especially for problems that depend on several input variables. Additionally, case-based reasoning is particularly vulnerable to the effect of data noise. Input data distorted by the presence of artifacts can baffle the analysis system's attempt to find a matching comparison case in the data base.

Artificial neural networks (ANNs) have held particular promise as an artificial intelligence tool for modeling steam generator tube integrity. ANN techniques have been applied to the eddy current identification of flaws in flat plates, and similar neural network defect-identification studies using tubes with machined flaws have been performed. Researchers have used ANNs to characterize the defect depth and artifact type for tubes with drilled holes and artifacts such as tube supports, copper, and magnetite. Employing this same drilled-hole data, others have applied ANNs to eddy current signal analysis for defect classification and for defect sizing. In order to separate EC crack signals from those due to the artifacts, a reference signal was subtracted from the test signal, where the reference signal was obtained from a tube without holes. Accordingly, the common features of the two EC measurements were removed, and the hole effects in the test signal were enhanced. The earlier research was later extended to estimate the depth of laboratory-generated outer-diameter stress corrosion cracks in simulated steam generator tubes. Despite these limited successes in classifying and sizing defects, this research has not translated into a predictive capability that allows modelers to accurately assess the integrity of a damaged tube.

More recently, researchers have proposed a hybrid system that combines rule-based logic, fuzzy syntactic pattern recognition techniques, and artificial neural networks for the detection and basic classification of flaws from eddy current signals. Similarly, others are developing a hybrid eddy current diagnostic system. However, these systems have yet to address the issue of distinguishing crack signals from other signal sources, nor do they attempt to quantify tube burst pressure, which is a more accurate predictor of tubing integrity.

It is therefore an object of the present invention to provide an improved method for assessing the physical integrity of a tube having a defect.

It is another object of the present invention to provide a novel method for predicting the burst pressure of a tube.

It is yet another object of the present invention to provide an improved method for more accurately assessing the integrity of a damaged tube.

It is a further object of the invention to provide a novel method for predicting the burst pressure of a tube having a critical tubing defect from inspection data of the critical tubing defect.

Other objects and advantages of the invention will become apparent by review of the detailed description of preferred embodiments.

SUMMARY OF THE INVENTION

In one form of the present invention, a method for predicting the integrity of a tube is provided. The present technique correlates a signal feature or features of raw inspection data of the tube with a range of burst pressures. In another form of the invention, the raw inspection data from the tube can be deconvolved into Gaussian peaks which, when combined, represent separate tubing defects. The critical tubing defect is then selected from the combined Gaussian peaks and correlated with a range of burst pressures for the critical tube defect.

The present method is preferably executed by collecting inspection data, such as EC data, on tubing having a defect, typically a crack, and deconvolving the inspection data into at least one undistorted defect signal. Deconvolution of the inspection data for a crack defect preferably comprises: fitting Gaussian peaks to the root mean square voltage-versus-axial-position curve of a test frequency of the inspection data; performing a least-squares fit of one of a horizontal and vertical voltage measurement data set for the test frequency of the inspection data utilizing the fit Gaussian peaks to determine the approximate axial peak location from the root mean square voltage-versus-axial-position curve of the test frequency; fitting further Gaussian peaks to remaining horizontal and vertical inspection data of the test frequency utilizing the least-squares fit of the one of a horizontal and vertical voltage measurement for the test frequency of the inspection data as a reference point; identifying matching sets of Gaussian peaks by comparing voltage-versus-position plots of the least-squares fit of the one of a horizontal and vertical voltage measurement for the test frequency of the inspection data; and constructing Lissajous plots of the matching pairs of Gaussian peaks wherein each Lissajous plot defines a separate undistorted anomalous signal, which may result from a tubing defect or artifact. The process is repeated for other EC test frequencies. The undistorted defect signal associated with the critical tubing defect is selected from the set of all of the deconvolved undistorted signals and is associated with a range of burst pressures through a regression technique, preferably utilizing an ANN.

The above described objects and embodiments are set forth in the following description and illustrated in the drawings described hereinbelow.

DETAILED DESCRIPTION OF THE PREFERRED EMBODIMENTS

Figure 1:
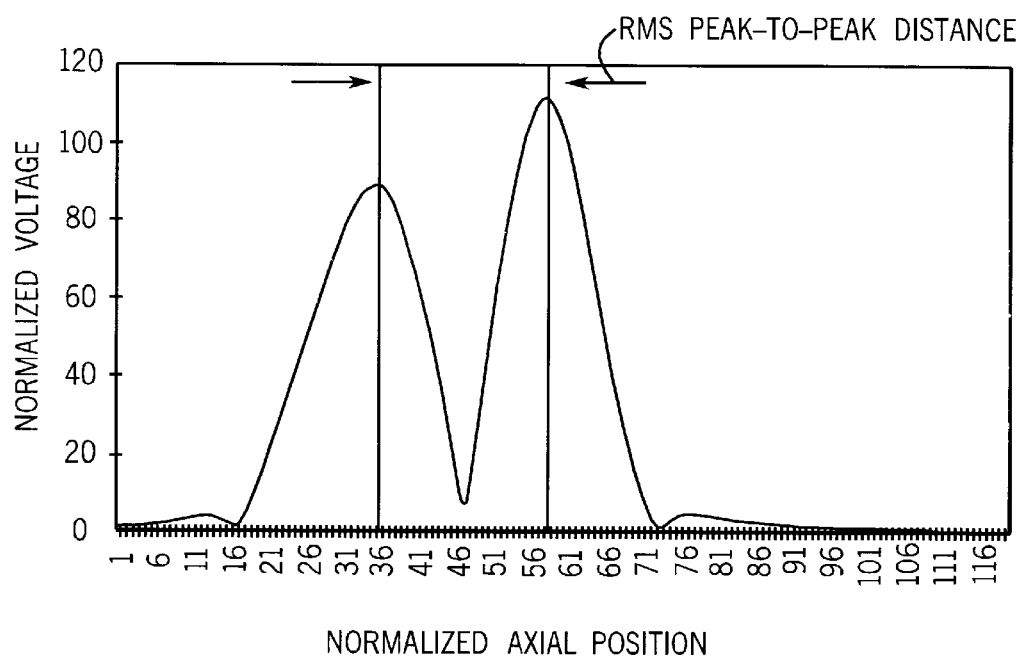
FIG. 1 illustrates the root mean square (RMS) peak-to-peak distance and RMS area for crack peaks of 100 kHz RMS inspection data.

In one form of the invention a method for predicting the burst pressure of tubing having a critical tubing defect is described which correlates a feature or features of raw tubing inspection data with a range of burst pressures utilizing a regression technique. In a preferred form of the present invention a novel signal processing technique is described which deconvolves raw eddy current signals into separate Gaussian peaks that represent signal contributions from different sources. Signals associated with the dominant crack are identified from the individual peaks, and the deconvolved signal features associated with the critical tubing defect are used to predict the burst pressure of the tube.

In one preferred form of the present invention, EC data collected via a differential bobbin-probe from a tube having a critical tubing crack is deconvolved into independent Gaussian curves. The deconvolution technique attempts to restore the full, undistorted crack signal. Identification of peaks associated with cracks allows EC signal features to be correlated to tube burst pressure through ANN modeling. A person skilled in the art will realize that this technique may also be performed in a similar manner on tube inspection data gathered through other probes (e.g. rotating-pancake-coil probes, pancake array probes, cross-wound coil probes, transmit/receive reflection coils, and guided wave bore probes) and techniques, including, but not limited to, bulk wave ultrasonic or other acoustical techniques or methods. The preferred embodiments of the present invention focus on deconvolution of EC bobbin coil probe data because EC bobbin coil probes are currently the predominant technology used for in-service inspection of nuclear power plant steam generator tubing.

According to signal processing theory, specific, associated sets of Gaussian curves represent different signal sources: e.g., tube support plates, cracks, deposits, and dents. Thus, the source of a signal can be determined based on the shape and position of the Lissajous pattern for each Gaussian curve and its phase rotation with test frequency.

The preferred EC voltage deconvolution technique is based on the following premises:

1. Each physical feature of the tube (e.g., a crack, a tube support plate, or a dent) has a corresponding set of peaks in the RMS voltage plot, although the composite set of peaks may obscure one another;
2. The full width at half maximum (FWHM) value of the individual peaks is limited by the resolution of the differential bobbin-coil probe, which is determined by the spacing of the two coils; and
3. The peaks associated with tubing cracks have characteristics (e.g., how their Lissajous patterns rotate with frequency) that identify them as crack peaks.

Once EC voltage signals have been normalized based on tube-standard measurements, commercially available software can be used to deconvolve the voltage traces. Each tube of a bobbin-probe eddy current inspection has associated with it several EC voltage curves, including at least: one vertical and one horizontal trace for each of the ac test frequencies (e.g., 400, 200, and 100 kHz); and one RMS voltage curve for each frequency.

Figure 2:
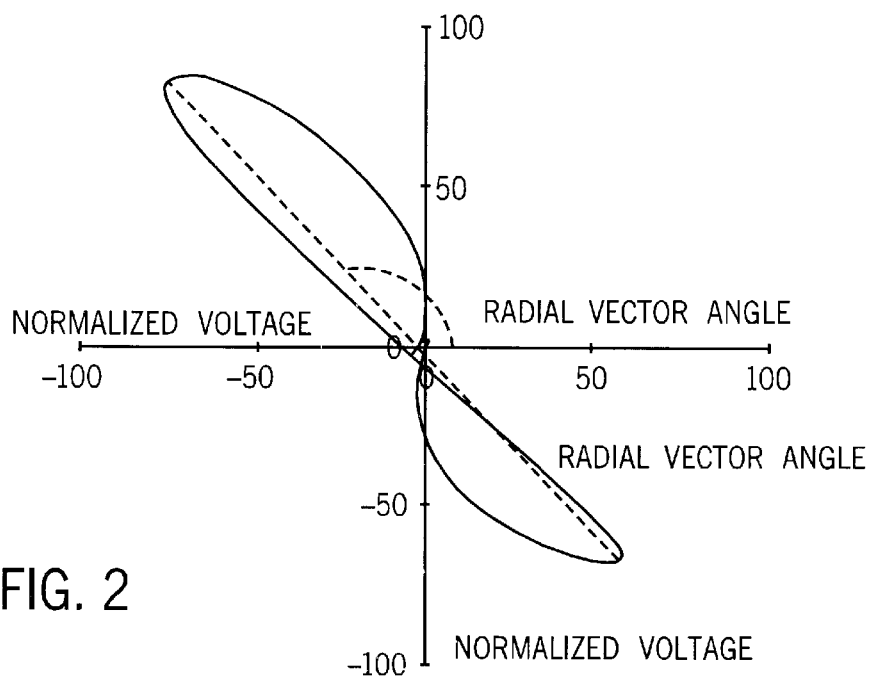
FIG. 2 illustrates the radial vector angle and radial vector length signal features of a Lissajous pattern.
Figure 3:
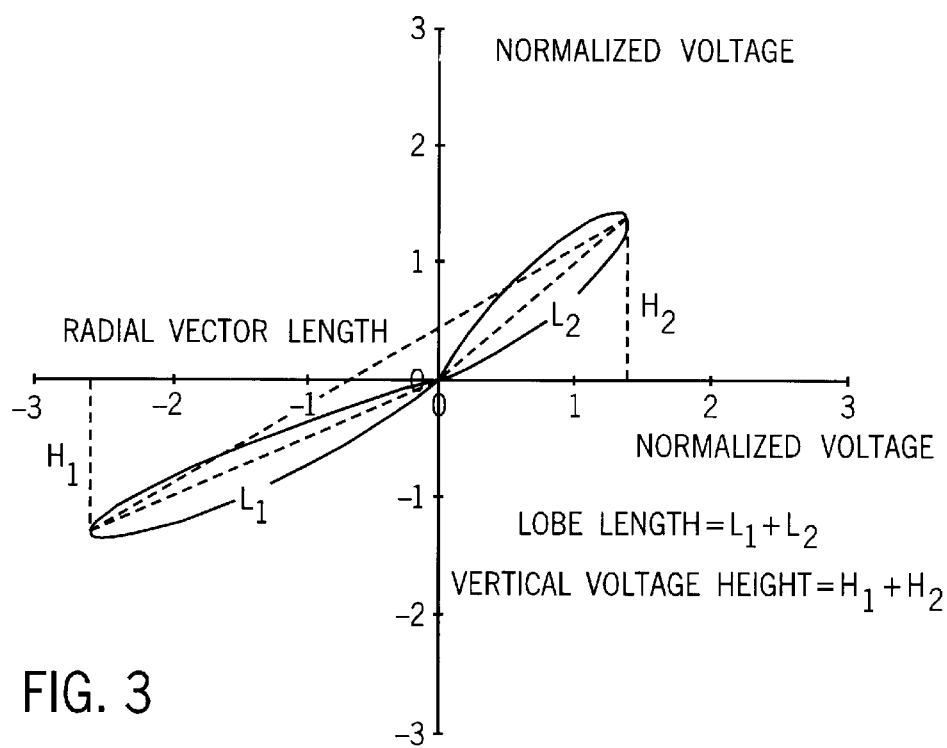
FIG. 3 illustrates the lobe length and vertical voltage height signal features of a Lissajous pattern.

Twenty-two EC signal features were considered for developing ANN burst pressure models in the Examples below:

1. 400 kHz RMS area for crack peaks;
2. 200 kHz RMS area for crack peaks;
3. 100 kHz RMS area for crack peaks;
4. RMS peak-to-peak distance (axial defect length);
5. 400 kHz radial vector length;
6. 200 kHz radial vector length;
7. 100 kHz radial vector length;
8. 400 kHz vertical voltage height;
9. 200 kHz vertical voltage height;
10. 100 kHz vertical voltage height;
11. 400 kHz Lissajous lobe length;
12. 200 kHz Lissajous lobe length;
13. 100 kHz Lissajous lobe length;
14. 400 kHz radial vector angle;
15. 200 kHz radial vector angle;
16. 100 kHz radial vector angle;
17. Radial vector angle change from 400 kHz to 200 kHz;
18. Radial vector angle change from 400 kHz to 100 kHz;
19. Radial vector angle change from 200 kHz to 100 kHz;
20. Radial vector length change from 400 kHz to 200 kHz;
21. Radial vector length change from 400 kHz to 100 kHz;
22. Radial vector length change from 200 kHz to 100 kHz;

The EC signal feature data were normalized from 0 to 1 to treat all input features equally in the ANN model. FIGS. 1–3 illustrate the definitions of the various features. Signal features based on the EC Lissajous patterns (features 5 through 22) are derived from the coordinates of the crack lobe ends.

For any given tube, the following procedure is preferably used to identify the Lissajous lobes for the critical crack:

1. The fitting software is used to roughly fit Gaussian peaks to the RMS voltage-versus-axial-position curve of one of the EC test frequencies (e.g., either 400, 200, or 100 kHz). Note that the RMS curves, created from the root mean square of the horizontal and vertical voltage readings, have only positive values, so only positive Gaussian peaks are required to fit the RMS curves. This greatly simplifies generating a rough fit, which determines the number of Gaussian peaks and the approximate axial locations of the Gaussian peaks along the tube. This initial RMS fit provides the basis for the fitting of one of the various vertical or horizontal voltage traces.
2. A least-squares fit of one of the horizontal or vertical voltage measurements for one of the test frequencies is performed using the previous RMS curve fitting to give the approximate axial locations of the peaks. This fit may include both positive and negative Gaussian curves. New peaks are added as needed to reduce the residuals between the fit and the original data.
3. The remaining horizontal and vertical voltage readings are fit using the previous fit results as a starting point. During the optimization of these fittings, the Gaussian peak widths are preferably held constant. Accordingly, only peak amplitudes and axial positions are allowed to change.
4. By comparing the voltage-versus-position plots of the combined set of Gaussian curves that constitute the fit of each horizontal and vertical inspection data, matching pairs of Gaussian peaks are identified. Each horizontal/vertical pair represents a separate Lissajous-figure lobe. (Note that combinations of more than one horizontal or vertical Gaussian peak may be required to define the Lissajous lobe.)
5. Lissajous plots of the horizontal/vertical peak pairs are constructed for each EC test frequency, creating a series of Lissajous lobes. Pairs of lobes that correspond to a single physical feature of the tube are matched by observing the phase angle change of the lobes with frequency. Ideally, matching lobe pairs form a figure-eight design. Often, however, the patterns are distorted. Lobe pairs are identified as signals from tube support plates, cracks, or other sources based on expert rules concerning their shapes and their dependence on frequency.

A Lissajous lobe pair is identified as the signal from the dominant tubing crack and provides the basis for EC signal features used for ANN testing and training. Expert rules are required to determine the best peak fit for the EC voltage signal and to select the combination of fitted peaks that represents the critical tube flaw. For example, the two lobes for an axial crack are expected to be approximately 180° apart and should have the same phase-angle rotation as the test frequency is increased.

Figure 4:
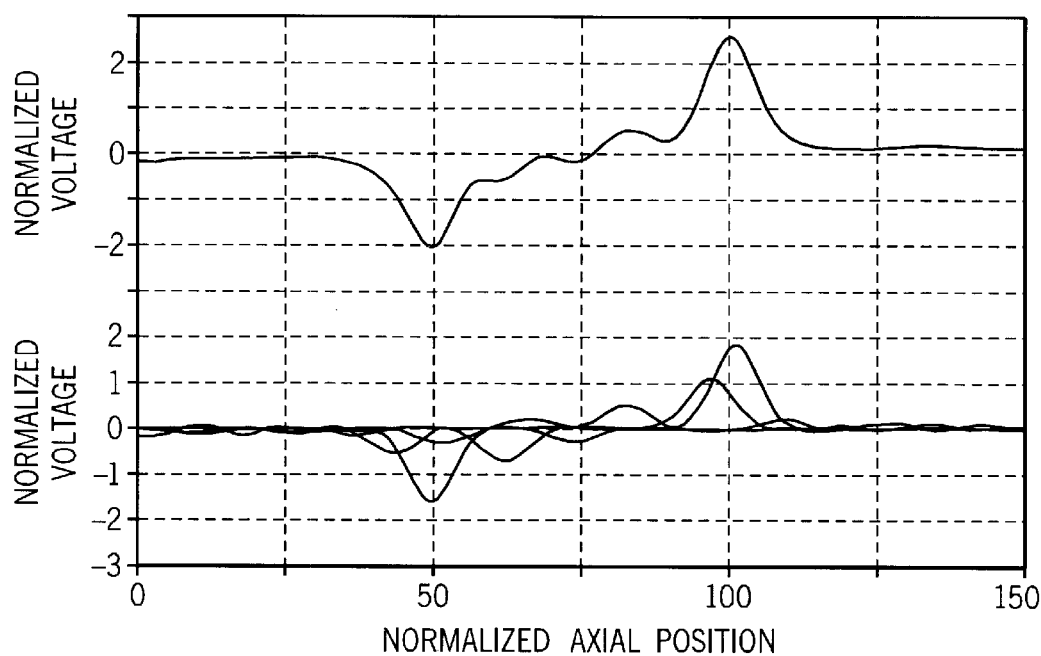
FIG. 4 illustrates the deconvolution of raw EC inspection data into a set of Gaussian peaks.
Figure 5:
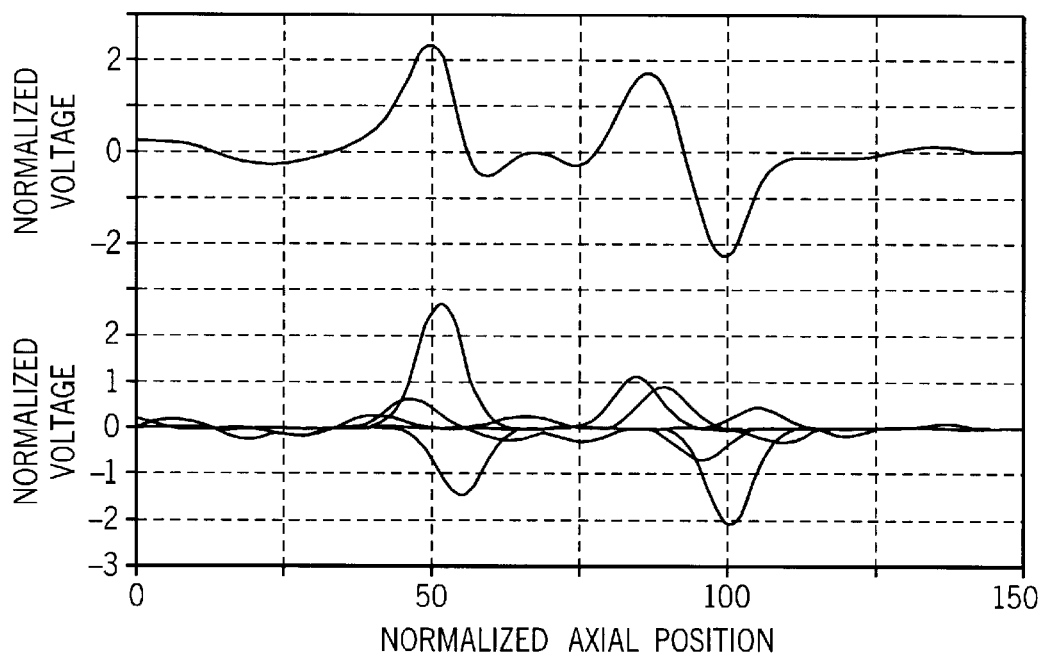
FIG. 5 likewise illustrates the deconvolution of raw EC inspection data into a set of Gaussian peaks.
Figure 6:
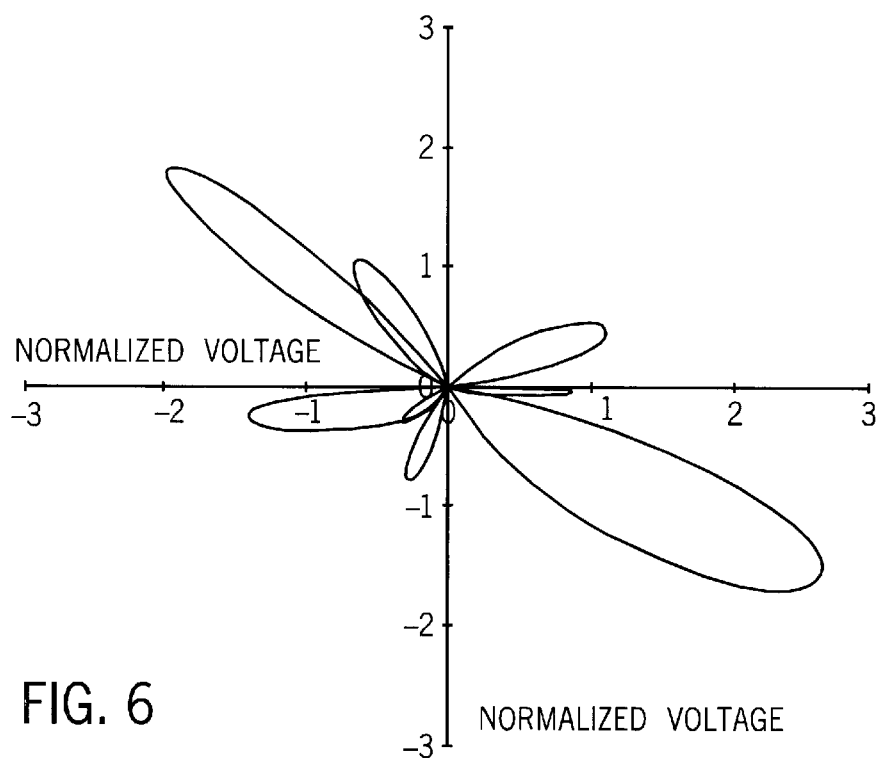
FIG. 6 illustrates Lissajous lobes for matching vertical and horizontal Gaussian peaks from the deconvolved Gaussian peaks of FIGS. 4 and 5.
Figure 7:
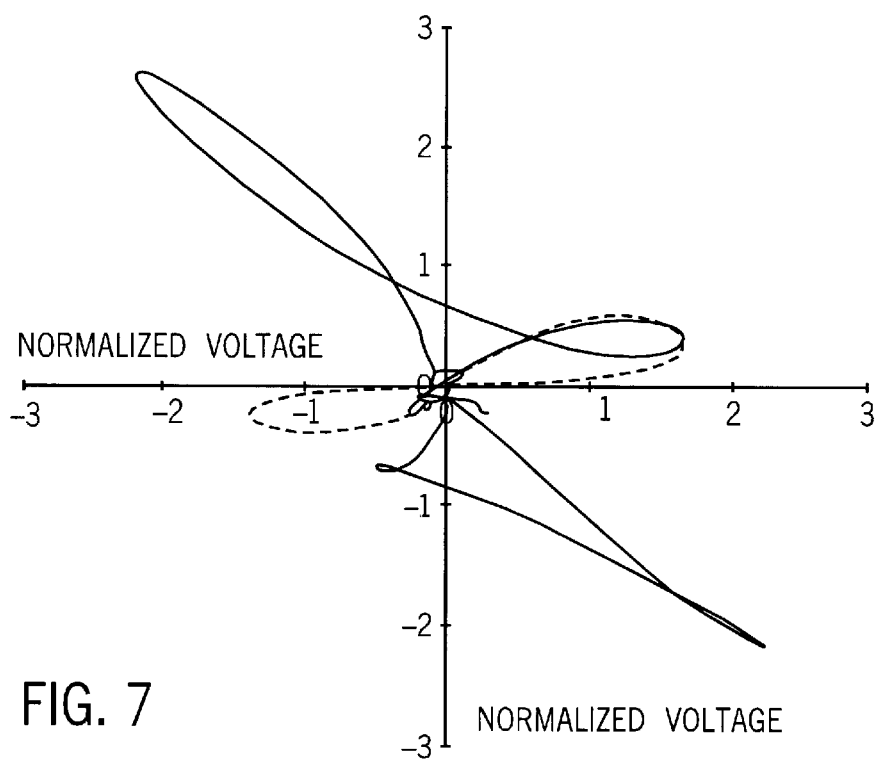
FIG. 7 illustrates a Lissajous lobe for a critical tubing crack from the combination of deconvolved EC inspection data of FIGS. 4 and 5 superimposed on a Lissajous pattern.

As an example, FIGS. 4 through 7 give the deconvolution results for the 400 kHz EC measurement of a cracked tube pulled from service at an operating nuclear power station. Field data often have more complicated Lissajous patterns than this, but the example serves to illustrate the deconvolution technique. FIGS. 4 and 5 show the set of deconvolved Gaussian curves used to fit the vertical and horizontal EC voltage signals. PeakFit Version 4 (SPSS, Inc.) software was used to perform these Gaussian curve fits. In each figure the lower plot shows the individual Gaussian peaks; the upper plot compares the combined set of Gaussian peaks to the original voltage signal. Twenty-one Gaussian peaks were used for both the vertical- and horizontal-signal curve fits. A series of Lissajous lobes were constructed from matching pairs of vertical and horizontal peaks located at the same axial position (FIG. 6). The Lissajous diagram represents a plot of vertical versus horizontal voltage at each axial position. A combination of lobes was selected as associated with a critical tubing crack (FIG. 7). Note that the selected lobes (dashed lines) do not directly correspond to positions on the original Lissajous pattern (solid line). Instead the measured crack-related lobes were distorted by the presence of the tube support plate edge near the crack tips.

The following non-limiting Examples set forth below employed PeakFit, Version 4 (SPSS, Inc.) software to fit the EC voltage signals with independent Gaussian curves. Peak-Fit determines the least-squares fit of a series of peaks to a data set.

EXAMPLE I

The data set for Example I used tubes with cracks grown within a simulated steam generator environment. The inspection data included, along with the EC readings, measurements of the pressure required to rupture the tubes at room temperature. The inspection data used in this Example covered fourteen tubes.

The 7/8-inch outside-diameter Alloy 600 tubes were fit with collars along their axis to simulate various tube support plate configurations and were packed with simulated steam generator sludge. The tubes were exposed to an aggressive environment in an experimental facility to promote accelerated cracking. In most cases, the tubes developed cracks with complete penetration through the tube wall at the collars. Bobbin probes were used to collect EC signals through the cracked regions. Afterward, the tubes were removed from their collars, burst-pressure tested and destructively examined. The burst pressure tests were performed at room temperature using an air-driven differential piston water pump. The reported burst pressures were normalized to account for the differing room-temperature flow stresses of the Alloy 600 lots. The flow stress is defined as the average of the yield and ultimate tensile strengths.

All tube cracks originated on the outer (OD) tube wall and were, in general, oriented axially along the tube, which is typical of stress corrosion cracking in operating steam generators. The crack morphologies ranged from single axial cracks to interconnected networks of small cracks. These various crack geometries complicated the description of the cracking by a single measure, such as crack length or crack depth.

The EC inspection data consisted of differential bobbin-probe voltage signals taken along the axis of each tube at four test frequencies (400, 200, 100, and 10 kHz). An ac frequency of 10 kHz gives a penetration depth far deeper than the thickness of a steam generator tube wall. Although EC readings taken at this frequency are useful in quickly locating tube support plates and other structures, their use in identifying and characterizing tube defects is minimal. Thus, the method provided by the preferred embodiments of the present invention was based on the other 400, 200 and 100 kHz frequencies. The amplitudes of the voltage signals for the fourteen tubes were normalized and their phases rotated based on EC measurements of tubes with standard notches.

In this Example I analysis of the inspection data, signal features that could be used as artificial neural network input variables were extracted directly from the original eddy current readings. That is, the deconvolution technique was not applied to the data. The candidate signal features included the radial vector lengths and radial vector angles for each of the three ac test frequencies along with numerous other Lissajous-pattern characteristics. The results showed that without the deconvolution technique, only twelve of the fourteen tubes could be adequately modeled.

For this example, feed-forward artificial neural networks were trained using software that employs the method of conjugate gradients to improve the learning process. ANN testing was performed with a separate program. Parametric studies were performed to determine which combination of features best predicted tubing burst pressure. In all cases, a leave-one-out (single-dropout) cross-validation technique was used to assess the ANNs. In addition to examining various EC signal features, the parametric studies also considered the dependence of the burst pressure predictions on the ANN architecture (i.e., on the number of hidden layers and the number of nodes in each hidden layer). Furthermore, the ANN models were optimized in terms of the fixed convergence criterion selected or, alternatively, in terms of the fixed number of training iterations. The standard deviation of the residuals between the ANN-predicted burst pressures and the measured burst pressures was used to judge the quality of each ANN.

Figure 8:
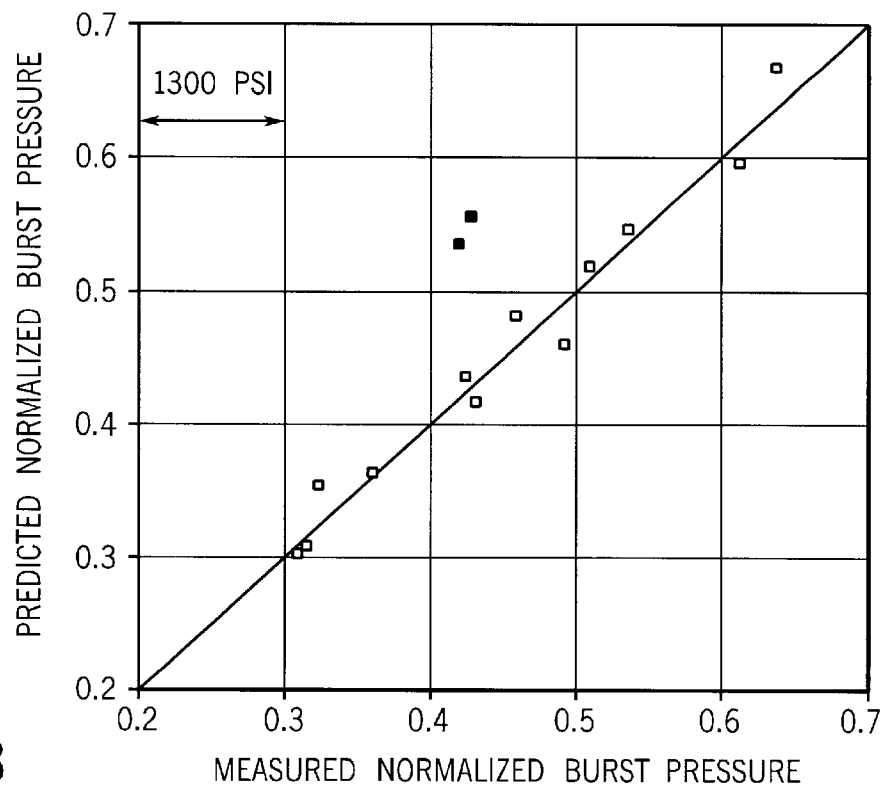
FIG. 8 is a plot of predicted burst pressure versus measured burst pressure from Example I.

The parametric studies showed that the best ANN models required five EC signal features as input variables: radial vector length for either 100 kHz or 200 kHz; RMS peak-to-peak distance (axial defect length); 400 kHz radial vector angle; 200 kHz radial vector angle; and angle change from 400 kHz to 200 kHz. The studies showed that two of the fourteen tubes had less than optimal ANN predictions. These outliers were removed from the ANN training set. A plot of predicted burst pressure versus measured burst pressure is presented in FIG. 8. In FIG. 8, each open symbol represents the ANN prediction of a tube when the model was trained using the remaining eleven tubes. The leave-one-out cross-validation standard deviation (calculated for the residuals of the ANN-predicted burst pressures versus the known burst pressures) was 258 psi, an error on the order of 4%. The worst burst pressure prediction residual was less than 450 psi. This result is a substantial improvement over previous reported attempts to predict tubing burst pressure from EC inspection signals.

The solid symbols in FIG. 8 are the predictions for the outlier tubes using an ANN trained with the remaining twelve tubes. In both cases, the ANN model greatly over-predicted the burst pressure—by up to 1650 psi. As shown in Example II, the explanation for these outliers is that the crack-related Lissajous-pattern lobes could not be correctly identified from the eddy current voltage data without the peak deconvolution technique.

EXAMPLE II

Figure 9:
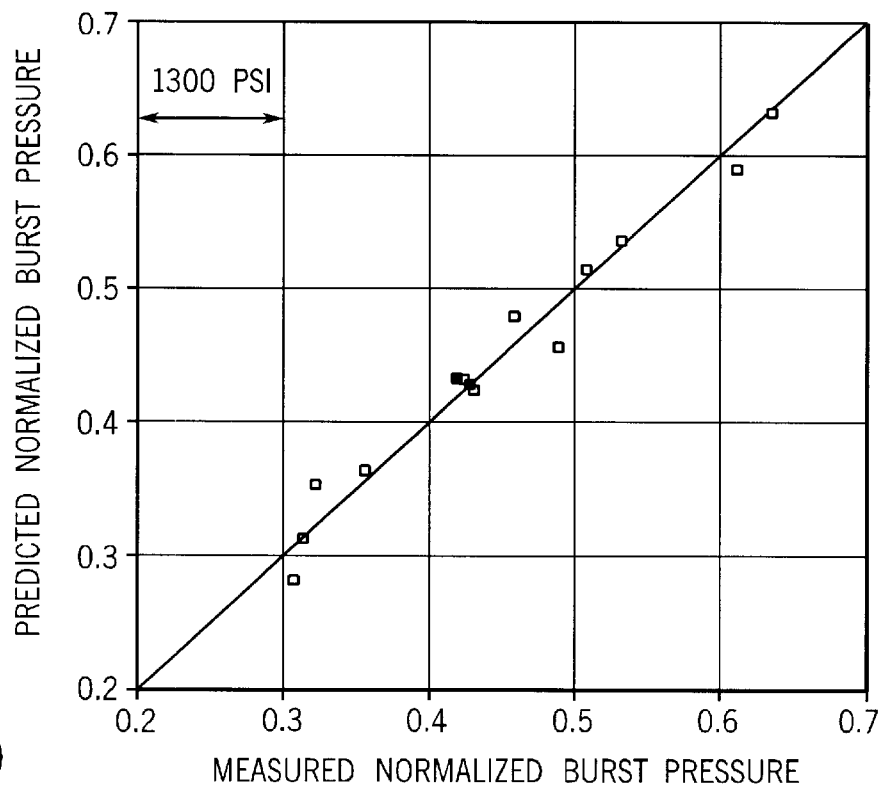
FIG. 9 is a plot of predicted burst pressure versus measured burst pressure from Example II.

Example II demonstrates how the deconvolution technique can improve the prediction of tube burst pressure. The inspection data of Example I were analyzed using the eddy current signal deconvolution procedure described above. Signal features were extracted from the Lissajous-pattern crack lobes generated through the deconvolution technique. ANNs were trained and tested using the same EC signal features as determined through the earlier parametric studies discussed in Example I. A new parametric analysis was used to determine the optimal ANN architecture and convergence criterion. The best ANN architecture, having eight nodes in a single hidden layer with a fixed convergence criterion of 360 psi, had a single-dropout standard deviation of 236 psi (FIG. 9), an improvement of 22 psi over the ANNs based on the raw (un-deconvolved) inspection data of Example I. More significantly, the two tubes that were dismissed as outliers in the Example I were successfully predicted by the new ANNs. That is, signal deconvolution resulted in a more accurate identification of the critical crack in the EC signals, which allowed for a better ANN analysis.

Figure 10:
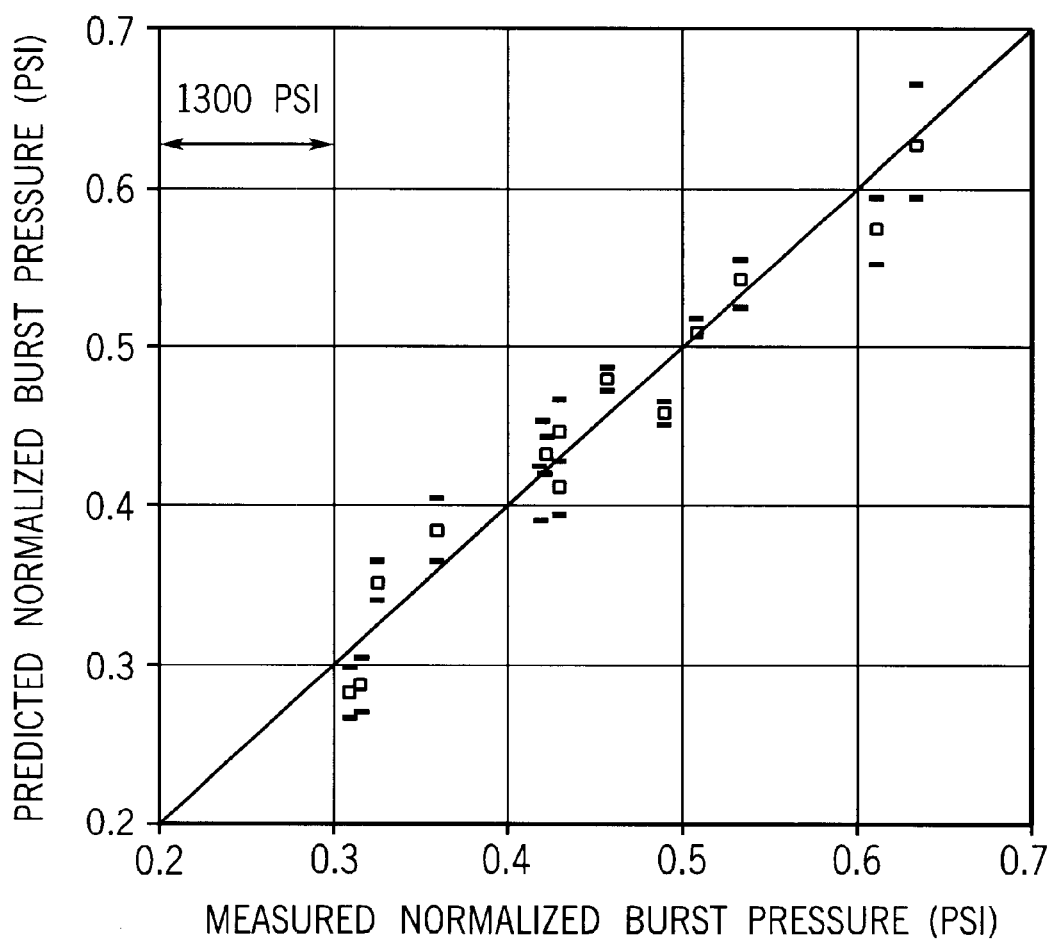
FIG. 10 is a plot of predicted burst pressure versus measured burst pressure from Example II showing mean predictions and one standard deviation for each dropout tube.

A multiple-dropout analysis was also performed for the final ANN architecture. One hundred ANN models were created from training sets of fourteen randomly selected tubes created from the original fourteen tubes. Each model was tested on the remaining tubes not used for training. The results are presented in FIG. 10, which displays the mean predictions and one standard deviation for each dropout tube. The standard deviation of the residuals of the mean predictions was 299 psi. In comparison, the multiple-dropout standard deviation for the ANNs using un-deconvolved data was 384 psi. This result demonstrates that the final ANN modeling is robust. Predictions were still good even when training was based on very few tubes. Notable in FIG. 10 are the results of the two tubes previously identified as outliers. The burst pressure estimates were consistently accurate even with multiple dropouts in the training set. This improvement in modeling performance was possible once a proper identification of the crack-related Lissajous-pattern lobes could be made through the peak deconvolution technique.

EXAMPLE III

The inspection data for this Example (the Pulled-Tube Burst Pressure inspection data) included bobbin probe EC measurements from 7/8-inch steam generator tubes removed from service at different operating nuclear plants. All tubes had a 7/8-inch outer diameter and were made from various heats of Alloy 600 with differing mechanical properties. The differing mechanical properties of the tubes were accounted for by normalizing the burst pressure to the room-temperature flow stress of the alloy, where the flow stress is defined as the average of the yield and the ultimate tensile strengths. The tubes, which all had defect indications near tube support plates, were burst-pressure tested using pressurized water within plastic bladders and then destructively examined. The Inventors did not have access to the examination results. The tubes had no support plate restraints during burst testing. The reported burst pressures were normalized based on a flow stress of 75 ksi. All tubing cracks originated in the outer diameter tube wall and were reported to be oriented axially along the tube. The cracks were generally shallower than the cracks in the data of Examples I and II.

Nine data files of 7/8-inch tubes from two nuclear plants were utilized in the final ANN model. Two outlier tubes from one plant had consistently poor ANN burst pressure predictions and were excluded from further study. Parametric studies were performed to determine which combination of features best predicted tubing burst pressure. In addition, parametric studies considered the dependence of the burst pressure predictions on the ANN architecture. Furthermore, the ANN models were optimized in terms of the fixed convergence criterion selected or, alternatively, in terms of the fixed number of iterations.

Only one EC signal feature was found to correlate to the flow-stress adjusted burst pressures of the nine selected Pulled-Tube cases: the 400 kHz radial vector angle (RVA). Better correlations than those achieved by previous researchers were obtained by relating the 400 kHz RVA and the yield strength to the measured non-adjusted burst pressures. This implies that the flow stress was not the best measure of the crack resistance of the tube, and accordingly, was not the best measure for accounting for varying mechanical properties among Alloy 600 lots. Rather, the ANNs were able to use the yield strength to determine an improved compensation for differing mechanical properties.

Figure 11:
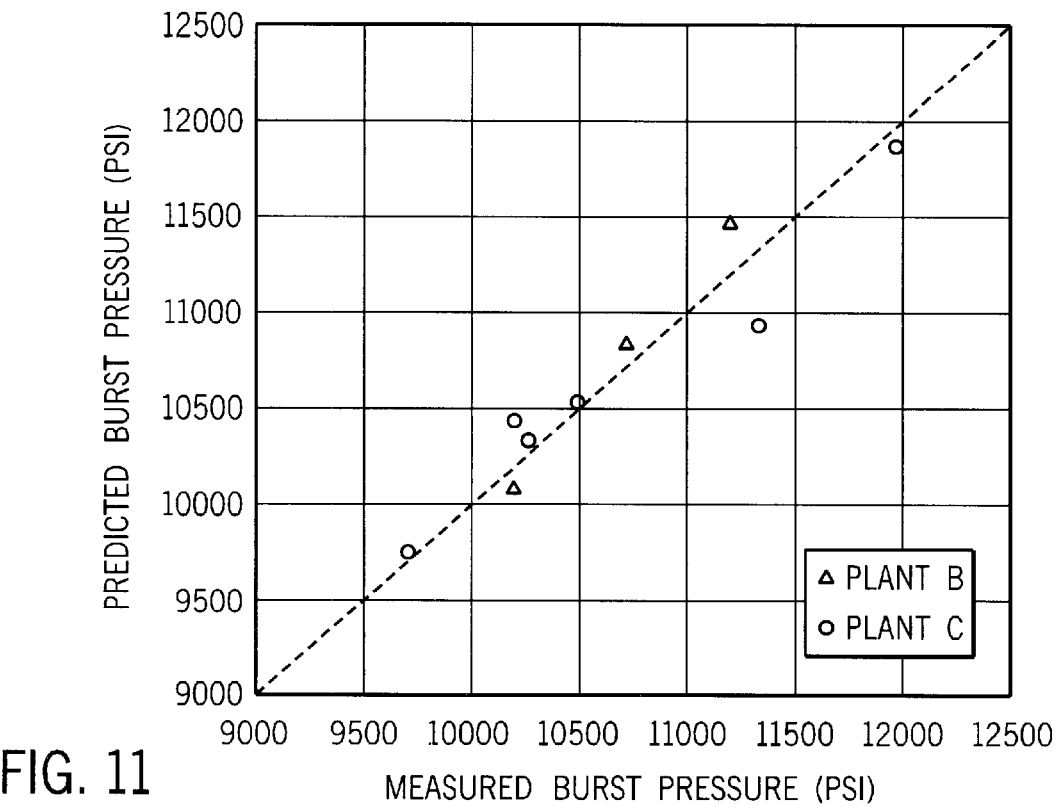
FIG. 11 is a plot of predicted burst pressure versus measured burst pressure from Example III.

The ANN architecture with the smallest standard deviation (213 psi) for a leave-one-out cross-validation analysis consisted of three nodes in a single hidden layer where the number of training iterations was fixed at nineteen. FIG. 11 shows a plot of the predicted burst pressures versus measured burst pressure. The worst burst pressure prediction deviates from the measured burst pressure by less than 500 psi. The standard deviations shown in this FIG. approach the inherent accuracy limit of burst pressure testing, meaning that the ANN model variability may in large part reflect the reproducibility of burst pressure testing, rather than modeling errors.

Figure 12:
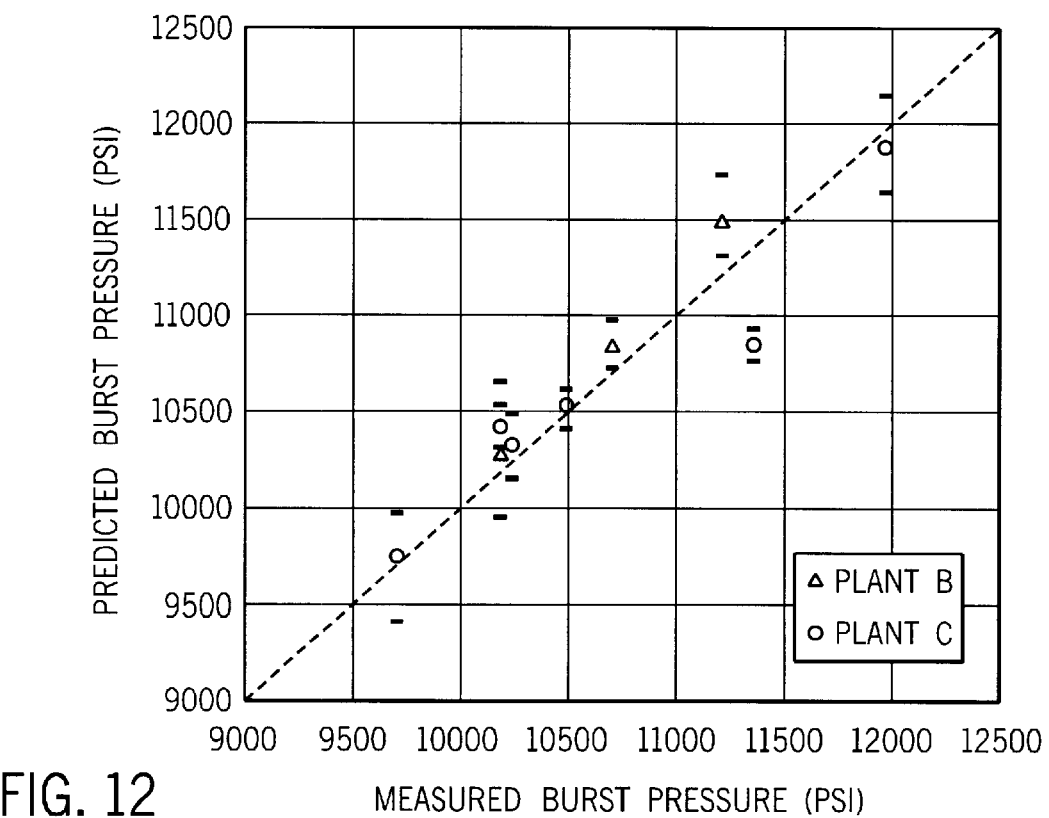
FIG. 12 is a plot of predicted burst pressure versus measured burst pressure from Example III showing mean predictions and one standard deviation for each dropout tube.

A multiple-dropout analysis was performed for the optimized Pulled-Tube ANN architecture. One hundred ANN models were trained from random training sets (each with nine tubes) created from the original nine tubes selected from the Pulled-Tube inspection data. Each model was tested on the remaining tubes not used for training. The results shown in FIG. 12 display the mean predictions and one standard deviation for each dropout tube. The standard deviation of the residuals of the mean predictions was 226 psi, only slightly greater than the single-dropout result of 213 psi. This indicates that the ANN model is robust. Even with a multiple number of tubes removed from the small data set, the model successfully predicted the burst pressure of the tubes within the data set.

While preferred embodiments have been illustrated and described, it should be understood that changes and modifications can be made therein in accordance with ordinary skill in the art without departing from the invention in its broader aspects. Various features of the invention are defined in the following claims.

What is claimed is:

1. A method for predicting the burst pressure of tubing having a critical tubing defect, comprising the steps of:

collecting inspection data on a tube having a critical tubing defect;

selecting a defect signal which corresponds to the critical tubing defect of the tube; and relating the selected undistorted defect signal of the critical tubing defect with a range of burst pressures.

2. The method of claim 1 wherein the inspection data comprises data collected by at least one of an electrical technique and an acoustical technique.

3. The method of claim 2 wherein the data collected by the electrical technique consists of eddy current data collected by a differential technique.

4. The method of claim 1 wherein the selected undistorted defect signal is related with a range of burst pressures by an artificial neural network.

5. A method for predicting the burst pressure of tubing having a critical tubing defect, comprising the steps of:

collecting inspection data on a tube having a critical tubing defect;

deconvolving the inspection data of the tube into at least one undistorted defect signal;

selecting the undistorted defect signal which corresponds to the critical tubing defect of the tube; and relating the selected undistorted defect signal of the critical tubing defect to a range of burst pressures.

6. The method of claim 5 wherein the inspection data comprises data collected by one of an eddy current technique and an acoustical technique.

7. The method of claim 6 wherein the data collected by the electrical technique consists of eddy current data collected by a differential technique.

8. The method of claim 5 wherein the selected undistorted defect signal is related with a range of burst pressures by an artificial neural network.

9. The method of claim 5 wherein the step of deconvolving the inspection data of the tube into at least one undistorted defect signal for all test frequencies of the inspection data comprises the steps of:

fitting Gaussian peaks to the root mean square voltage-versus-axial-position curve of a test frequency of the inspection data;

performing a least-squares fit of one of a horizontal and vertical voltage measurement for the test frequency of the inspection data utilizing the fit Gaussian peaks to determine the approximate axial peak location from the root mean square voltage-versus-axial-position curve of the test frequency;

fitting further Gaussian peaks to remaining horizontal and vertical inspection data of the test frequency utilizing the least-squares fit of the one of a horizontal and vertical voltage measurement for the test frequency of the inspection data as a reference point;

identifying matching sets of Gaussian peaks by comparing voltage-versus-position plots of the least-squares fit of the one of a horizontal and vertical voltage measurement for the test frequency of the inspection data and the fitted further Gaussian peaks; and constructing Lissajous plots of the matching pairs of Gaussian peaks wherein each Lissajous plot defines a separate signal that represents the undistorted defect signal of the critical tubing defect.

10. The method of claim 5 wherein the critical tubing defect comprises a crack.

11. A method for predicting the burst pressure of tubing having a critical tubing crack, comprising the steps of:

collecting eddy current data on a tube having a critical tubing crack;

fitting Gaussian peaks to the root mean square voltage-versus-axial-position curve of a test frequency of the eddy current data;

performing a least-squares fit of one of a horizontal and vertical voltage measurement for the test frequency of the eddy current data utilizing the fit Gaussian peaks to determine the approximate axial peak location from the root mean square voltage-versus-axial-position curve of the test frequency;

fitting further Gaussian peaks to remaining horizontal and vertical eddy current data of the test frequency utilizing the least-squares fit of the one of a horizontal and vertical voltage measurement for the test frequency of the eddy current data as a reference point;

identifying matching pairs of Gaussian peaks by comparing voltage-versus-position plots of the least-squares fit of the one of a horizontal and vertical voltage measurement for the test frequency of the eddy current data and the fitted further Gaussian peaks;

constructing Lissajous plots of the matching pairs of Gaussian peaks wherein each Lissajous plot defines a separate undistorted anomaly signal;

selecting the undistorted anomaly signal which corresponds to the critical tubing crack of the tube; and utilizing an artificial neural network to relate the selected undistorted crack signal of the critical tubing crack with a range of burst pressures.

* * * * *